United States Patent [19]
Potter

[11] Patent Number: 5,535,760
[45] Date of Patent: Jul. 16, 1996

[54] METHOD FOR DETECTING AND TREATING ALZHEIMER'S DISEASE

[75] Inventor: Huntington Potter, Boston, Mass.

[73] Assignee: President and Fellows of Harvard College, Cambridge, Mass.

[21] Appl. No.: 409,103

[22] Filed: Mar. 24, 1995

Related U.S. Application Data

[63] Continuation of Ser. No. 109,746, Aug. 20, 1993, abandoned, which is a continuation-in-part of Ser. No. 678,683, Apr. 1, 1991, Pat. No. 5,297,562.

[51] Int. Cl.$^6$ .................................................. A61B 19/00
[52] U.S. Cl. .................................................. 128/898
[58] Field of Search .................. 128/897–98; 424/9

[56] References Cited

PUBLICATIONS

B. Katz, et al., "Cholinergic Supersensitivity of the Iris Sphincter in Alzheimer's Disease," *Ophthal.*, 95:134 (Sep. 1988 Supp).

Sitaram, N. and Pomara, N., "Increased Pupillary Miotic Response to Pilocarpine in Cognitively Impaired Elderly Subjects," *ICRS Medical Science*, 9:409–410 (1981).

Potter, H., "Review and Hypothesis: Alzheimer Disease and Down Syndrome–Chromosome 21 Nondisjunction May Underlie Both Disorders," *Am. J. Hum. Genet.*, 48:1192–1200 (1991).

Inzelberg, R., et al., "Effects of Atropine on Learning and Memory Functions in Dementia," *Clinical Neuropharmacology*, 13(3):241–247 (1990).

Schweber, M. S., "Alzheimer's Disease and Down Syndrome," *Progress in Clinical and Biol. Research*, 317:247–267 (Alan R. Liss, Inc., 1989).

Lichter, P., et al., "Rapid Detection of Human Chromosome 21 Aberrations by in situ Hybridization," *Proc. Natl. Acad. Sci. USA*, 85:9664–9668 (1988).

Talamo, B. R., et al., "Pathological Changes in Olfactory Neurons in Patients with Alzheimer's Disease," *Nature*, 337:736–739 (1989).

Schweber, M., "A Possible Unitary Genetic Hypothesis for Alzheimer's Disease and Down Syndrome," *Anals of NY Acad. Sciences*, 450:223–238 (1985).

Madan, K. et al., "Premature Centromere Division (PCD): A Dominantly Inherited Cytogenetic Anomaly," *Hum. Genet.*, 77:193–196 (1987).

Jabs, E. W., et al., "Centromere Separation and Aneuploidy in Human Mitotic Mutants: Roberts Syndrome," *Mechanisms of Chrom. Dist. and Aneuploidy*, 111–118 (Alan R. Liss, Inc., 1989).

Uchida, I. A., et al., "Chromosome Aberrations Induced in vitryo by Low Doses of Radiation: Nondisjunction in Lymphocytes of Young Adults," *Am. J. Hum. Genet.*, 27:419–429 (1975).

Romke, C., et al., "Roberts Syndrome and SC Phocomelia. A Single Genetic Entity," *Clinical Genetics*, 31:170–177 (1987).

Moorhead, P. S., and Heyman, A., "Chromosome Studies of Patients with Alzheimer Disease," *Amer. J. Of Med. Genet.*, 14:545–556 (1983).

Evans, D. A., et al., "Prevalence of Alzheimer's Disease in a Community Population of Older Persons," *JAMA*, 262(18):2551–2556 (1989).

Jarvik, L. F., et al., "Chromosomes and Mental Status," *Arch. Gen. Psychiatry.*, 30:186–190 (1974).

Matsuyama, S. S., and Jarvik, L. F., "Hypothesis: Microtubules, a Key to Alzheimer Disease," *Proc. Natl. Acad. Sci. USA*, 86:8152–8156 (1989).

(List continued on next page.)

*Primary Examiner*—Angela D. Sykes
*Assistant Examiner*—John P. Lacyk
*Attorney, Agent, or Firm*—Hamilton, Brook, Smith & Reynolds

[57] ABSTRACT

The subject matter of this disclosure links Alzheimer's Disease with somatic mosaicism of cells trisomic for chromosome 21. Disclosed are methods of detecting Alzheimer's Disease in an individual by measuring certain characteristics known to be associated with Down syndrome that arise due to the trisomy nature of that disorder.

19 Claims, 1 Drawing Sheet

OTHER PUBLICATIONS

Nordenson, I., et al., "Chromosomal Abnormality in Dementia of Alzheimer Type," *The Lancet*, 481–482 (Mar. 1, 1989).

Buckton, K. E., et al., "Chromosome Changes in Alzheimer's Presenile Dementia," *J. of Med. Genet.*, 20:46–51 (1983).

Ward, B. E., et al., "Increased Aneuploidy in Alzheimer Disease," *Amer. J. of Med. Genet.*, 3:137–144 (1979).

White, B. J., et al., "Cytogenetic Studies of Familial and Sporadic Alzheimer Disease," *Amer. J. of Med. Genet.*, 10:77–89 (1981).

Heston, L. L., and Mastri, A. R., "The Genetics of Alzheimer's Disease," *Arch. Gen. Psychiatry*, 34:976–981 (1977).

Heston, L. L. et al., "Dementia of the Alzheimer Type," *Arch. Gen. Psychiatry*, 38:1085–1090 (1981).

Lai, F., and Williams, R. S., "A Prospective Study of Alzheimer Disease in Down Syndrome," *Arch. Neurol.*, 46:849–853 (1989).

Pagon, R. A., et al., "Abnormal Skin Fibroblast Cytogenetics in Four Dysmorphic Patients with Normal Lymphocyte Chromosomes," *Am. J. Hum. Genet.*, 31:54–61 (1979).

Goate, A. M., et al., "Predisposing Locus for Alzheimer's Disease on Chromosome 21," *The Lancet*, 352–355 (Feb. 18, 1989).

Peters, G. B., et al., "Trisomy 21 Mosaicism and Maternal Age Effect," *The Lancet*, 1202–1203 (May 23, 1987).

Robison, S. H., et al., "Alzheimer's Disease Cells Exhibit Defective Repair of Alkylating Agent–Induced DNA Damage," *Anals of Neurology*, 21(3):250–258 (1987).

Hardy, J., et al., "Presenile Dementia Associated with Mosaic Trisomy 21 in a Patient with a Down Syndrome Child," *The Lancet*, 743 (Sep. 23, 1989).

Rowe, I. F., et al., "Presenile Dementia Associated with Mosaic Trisomy 21 in a Patient with a Down Syndrome Child," *The Lancet*, 229 (Jul 22, 1989).

Harris, W. S. and Goodman, R. M., "Hyper–Reactivity to Atropine in Down's Syndrome," *N.E. J. of Med.*, 279(8):407–410 (1968).

Fitzgerald, P. H., et al., "Evidence for the Repeated Primary Non–Disjunction of Chromosome 21 as a Result of Premature Centromere Division (PCD)," *Hum. Genet.*, 72:58–62 (1986).

Sacks, B. and Smith S., "People with Down's Syndrome can be Distinguished on the Basis of Cholinergic Dysfunction," *J. of Neurology, Neurosurgery, and Psych.*, 52:1294–1295 (1989).

Berg, J. W., et al., "Atropine in Mogolism," *Lancet*, 2:441–442 (1959).

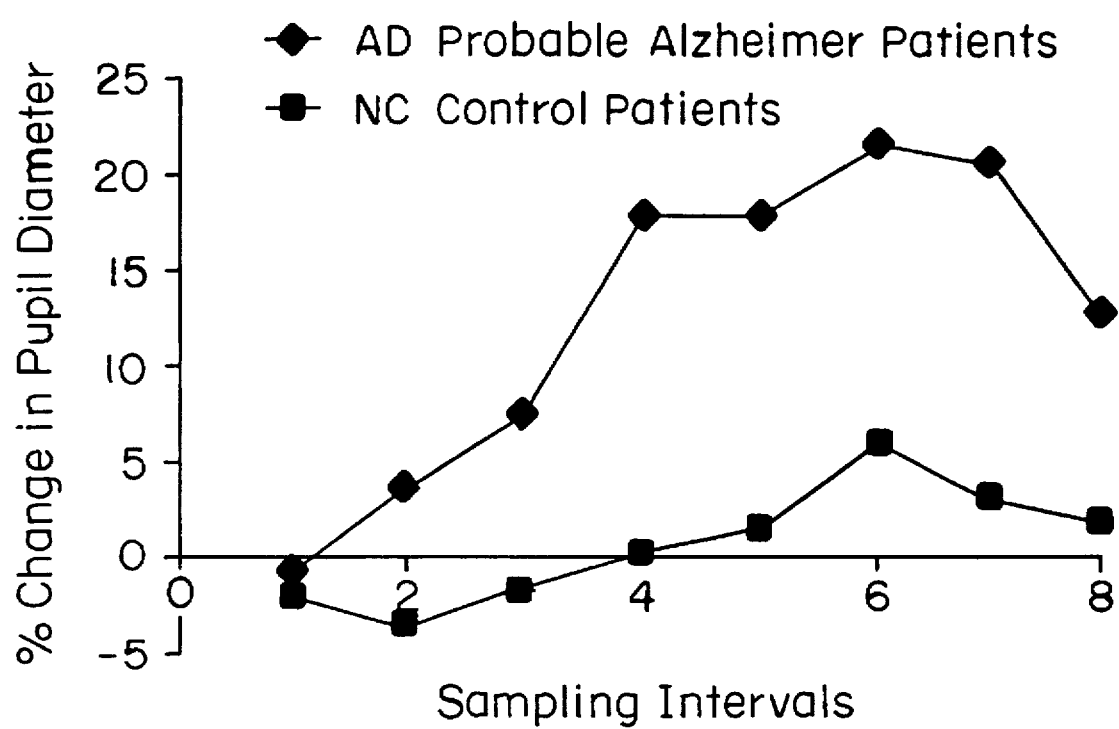

METHOD FOR DETECTING AND TREATING ALZHEIMER'S DISEASE

RELATED APPLICATION

This application is a continuation of application Ser. No. 08/109,749 filed Aug. 20, 1993 now abandoned, which is a Continuation-In-Part of U.S. Ser. No. 07/678,683 Apr. 1, 1991 now U.S. Pat. No. 5,297,562.

BACKGROUND OF THE INVENTION

It has been appreciated for some time that Alzheimer's disease has a complex etiology. At least 15 percent of the cases appear to be due to the inheritance of an autosomal-dominant mutation, but the majority are "sporadic", showing no clear association with any identifiable genetic or environmental factor. Feldman, R. G., et al., Neurology, 13:811–824 1963; Heston, L. L., et al., Arch Gen. Psychiat., 38:1084–1090 (1981); Terry, R. D., Aging, 7:11–14 (1978); Jarvik, L. F. and Matsuyama, S. S., "The Biological Substrates of Alzheimer's Disease", Academic Press, pp. 17–20 (1986). Even identical twins can show a large discordance in the age of onset of the disease. Nee, L. E., et al., Neurology, 37:359–363 (1987). Yet despite this variation, Alzheimer's disease shows a uniform set of clinical and pathological features progressive loss of memory and other intellectual functions beginning in middle to late life, coupled with neuronal cell loss in the higher centers of the brain. Price, D. L., Ann. Rev. Neurosci., 9:489–512 (1986).

When examined by histochemical stains, Alzheimer's disease brains, particularly the hippocampus, neocortex, and amygdala, exhibit certain neuropathological protein deposits that serve as the defining characteristic of the disease. One such deposit, termed the neurofibrillary tangle, occurs inside neurons and is composed of "paired helical" protein filaments (PHF). Because they can be found in other neurodegenerative diseases, paired helical filaments are likely to be a common feature of dying neurons. The more definitive lesion of Alzheimer's disease is the "neuritic or senile plaque", which consists of a spherical, extracellular core of filamentous protein material surrounded by a halo of degenerating nerve cell processes. Extracellular protein filaments similar to those seen in the cores of neuritic plaques also accumulate in the walls of meningeal and intracortical blood vessels. The deposits of protein filaments in the cores of neuritic plaques and in blood vessels are referred to by the generic term "amyloid".

The first identical constituent of Alzheimer amyloid deposits was purified from meningeal blood vessels and its sequence determined by Glenner, G. G. and Wong, C. W., Biochem. Biophys. Res. Commun., 122:1131–1135 (1984). This protein, termed β or A4, a is ~42 amino-acid-long fragment of a larger protein that is a normal constituent of the brain and other tissues. A second protein component of Alzheimer amyloid deposits was identified as the serine protease inhibitor $\alpha_1$-antichymotrypsin (ACT).

While much has been learned about the biochemistry and expression of the aberrant protein deposits that characterize Alzheimer's disease, progress toward the development of methods for the diagnosis and treatment of the disease has been slow. This is due, at least in part, to the fact that the molecular basis for the disease pathology has remained obscure.

SUMMARY OF THE INVENTION

The subject invention relates to a method for detecting Alzheimer's disease comprising testing an individual for the presence of a mosaic population of cells. The mosaic population of cells includes normal cells having two copies of chromosome 21 and abnormal cells which contain 3 copies of chromosome 21. The mosaicism can be detected, for example, by in situ hybridization or by detecting increased sensitivity to cholinergic agonists or antagonists.

The invention enables detection of early signs of Alzheimer's disease prior to the onset of dementia. Also disclosed are methods for preventing the onset of dementia in Alzheimer's disease.

BRIEF DESCRIPTION OF THE DRAWING

The FIGURE is a diagram representing results obtained in studies of mydriasis following tropicamide administration to one eye in each of five patients diagnosed as probable Alzheimer's patients and 13 negative control patients who did not exhibit symptoms characteristic of Alzheimer's Disease. FIG. 1 shows in graphical form the percent change in pupil diameter of the treated eye versus the untreated eye at eight different sampling intervals occurring at 0, 2.5, 8, 15, 22, 29 41 and 53 minutes. FIG. 1 also compares the change in pupil diameter of patient's diagnosed as probable Alzheimer's patients (-♦- AD) and patients without the symptoms characteristic of Alzheimer's Disease (-■- CN).

DETAILED DESCRIPTION OF THE INVENTION

Applicant's invention was made possible by the development of a mechanistic theory which provides cohesiveness to apparently disparate experimental results in Alzheimer's Disease research. A brief review of the literature is essential to an appreciation of the invention.

Perhaps the most interesting clue to the cause of Alzheimer's disease is the fact that Down syndrome patients who live beyond the age of 30 or 40 develop dementia and neuropathology essentially indistinguishable from classic Alzheimer's disease. Olson, M. I. and Shaw, C. M., Brain, 92:147–156 (1969); Glenner, G. G. and Wong, C. W., Biochem. Biophys. Res. Commun., 122:1131–1135 (1984); Wisniewski, H. M. and Terry, R. D., In: Ford DH (ed) Progress in Brain Research, 40:1108–1109 (1988). The implication of this finding is that trisomy for chromosome 21—the pathogenetic cause of Down syndrome—is also capable of causing Alzheimer's disease, possibly through the overexpression of a gene residing on chromosome 21. Schweber, M., Ann. NY Acad. Sci., 450:223–238 (1985).

On the other hand, almost all aged humans (and monkeys) develop some amyloid deposits which, by several criteria, appear to be identical to those that accumulate in much larger numbers and at an earlier time in Alzheimer's disease and Down syndrome (Wisniewski, H. M. and Terry, R. D., In: Ford DH (ed) Progress in Brain Research, 40:1108–1109 (1973); Selkoe, D. J., et al., Science, 235:873–877 (1987); Abraham, C. R. and Potter, H., Biotechnology, 7:147–153 (1989). Thus, any hypothesis for the pathogenesis of Alzheimer's disease should be able to explain not only the relation between the familial and sporadic forms of the disease but also how these are related to Down syndrome and to the "normal" process of aging.

The association between Alzheimer's disease and chromosome 21 has been reinforced by a number of recent clinical and experimental findings. These, and earlier results on the genetics, epidemiology, and cell biology of Alzheimer's disease, have been considered. In particular, its association with Down syndrome has been assessed.

A molecular basis for Alzheimer's disease, which is consistent with both the genetic and sporadic forms of the disease can be explained as arising from the accumulation of chromosome 21 trisomy cells during the life of the individual. That is, trisomy 21 cells, developing over time by unequal chromosome segregation during mitosis, may ultimately lead to Alzheimer's disease through the same (as yet unknown, and perhaps multistep) mechanism by which Down syndrome patients acquire the disease, but at a later age due to the modulating effect of the mosaicism.

The first specific model linking Alzheimer's disease to Down syndrome arose when the gene for the amyloid βprotein was cloned and found to be located on chromosome 21. Goldgaber, D., et al., *Science,* 235:877 (1987); Kang, J., et al., *Nature,* 325:733 (1987); Tanzi, R. E., et al., *Science,* 235:880 (1987); Robakis, N. K., et al., *Proc. Natl. Sci. USA,* 84:4190 (1987). The implication of these results seemed that accumulation of amyloid in Alzheimer's disease was caused by the overexpression of a routant β-protein gene or by a duplication of the β-protein gene on chromosome 21 that mimicked the gene-dosage effect of Down syndrome. The fact that some Alzheimer's disease families could be shown to harbor their autosomal dominantly-inherited mutation on chromosome 21 (St. George-Hyslop, P. H., et al., *Science,* 235:885–889 (1987)) and that the β-protein precursor gene was apparently overexpressed in Down syndrome (Tanzi, R. E., et al., *Science* 235:880 (1987); Neve, et al., 1988) further implicated the β-protein gene as a potential site for the disease locus.

Very recently, a variant form of the β-protein precursor gene encoding a mutant β-protein has been found in families with Hereditary Cerebral Hemorrhage with Amyloidosis of Dutch Origin, suggesting that this mutation may be the inherited defect in this disease (Van Broeckhoven, C., et al., *Science,* 248:1120–1122 (1990); Levy, E., et al., *Science,* 248:1124–1126 (1990). However, an early study suggesting that the β-protein gene existed in three copies in Alzheimer's disease patients was not confirmed. Also the pattern of expression of the β-protein gene was subtly altered in Alzheimer brain but not simply overexpressed (see Tanzi, R. E., et al., *Science* 235:880 (1987); Neve, R. L., et al., *Neuron,* 1:669–677 (1988); Palmert, M. R. et al., *Science,* 241:1080–1084 (1988); Higgins, G. A., et al., *Proc. Natl. Acad. Sci.,* 85:1297–1301 (1988); and Golde, T. E., et al., *Neuron* 4:253–267 (1990) for data and discussion of Alzheimer- and Down syndrome-specific changes in the expression of the several β-protein precursor mRNAs). Finally, the actual location of a potential Alzheimer's disease mutation on chromosome 21 in some families was soon shown to be far from the β-protein gene itself and closer to the centromere (Tanzi, et al., *Nature* 329:156–157 (1987b); Van Broeckhoven, et al., *Nature* 329:153–155 (1987); Goate, et al., *Lancet* Feb. 18:352 (1989)).

The finding in some families showing no linkage to any marker on chromosome 21 suggests that the inherited form of Alzheimer's disease is genetically heterogeneous (Schellenberg, et al., *Science* 241:1507–1510 (1988); St. George-Hyslop, et al., *Nature* 347:194–197 (1990)). Chromosome 19 (Roses, et al., *Adv. Neurol.* 51:185–196 (1990)) and possibly the region of chromosome 14 now known to be close to the ACT gene (Weitkamp, et al., *Amer. J. Hum. Genet.* 35:443–453 (1983); Rabin, et al., *Somatic Cell Mol. Genet.* 12:209–214 (1986)) have been proposed as candidate locations for the disease locus. These results indicate that an aberrant biochemical pathway leading to the Alzheimer neuropathology can be initiated by mutation in a number of genes, including one on chromosome 21, but not the β-protein precursor gene itself.

Chromosome 21 was further implicated in the etiology of Alzheimer's disease by the discovery that some families in which Alzheimer's disease is inherited as an autosomal dominant mutation produce a significantly higher-than-normal number of Down syndrome children (Heston and Mastri, *Arch. Gen. Psychiatry* 34:976–981 (1977); Heston, et al., *Arch. Gen. Psychiat.* 38:1084–1090 (1981); Heyman, et al., *Ann. Neurol.* 14:507–515 (1983)). In the first study, the total number of Down's cases was 11 out of 3,044 Alzheimer's disease relatives. The mothers' ages at the birth of their children were given as 21, 26, 30, 30, 35, 39, 40, 41 and 46, plus two unknown ages. The average maternal age (34) is higher than the average maternal age for all births, which is approximately 29. However, the results would still be significant if, for instance, the children of the two or three oldest mothers were not considered (the frequency of Down syndrome is 1.3 per thousand live births to mothers of all ages). The number of relatives analyzed in the second study was 1278, including 4 Down syndrome individuals conceived to mothers of ages 26, 31, 33, and 38. These numbers are small and the average maternal age is a little high, but even if the one case of age 38 were artificially removed, the results are also statistically significant. In contrast, other researchers have failed to confirm the increased incidence of Down syndrome in families with inherited Alzheimer's disease, but they report that the number of relatives they analyzed was too few for the lack of Down syndrome to be statistically significant (Whalley, et al., *Brit. J. Psychiat.* 140:249–256 (1982); Amaducci, et al., *Neurology* 36:922–931 (1986); Chandra, et al., *Neurology* 37:1295–1300 (1987)).

Recently, mouse chromosome 16, which is partially homologous to human chromosome 21, including the β-protein gene, has been shown to result, when trisomic, in neurodegeneration somewhat like that seen in Alzheimer's disease. Because mouse chromosome 16 is much larger and contains many more genes than does human chromosome 21, trisomy 16 mice suffer many developmental abnormalities and do not survive to term. However, the specific effect of this trisomy on the nervous system can be tested by transplanting embryonic brain tissue from a trisomy 16 embryo into the brain of a normal adult. When the brains of such host mice with their trisomy 16 grafts were examined, it was found that some of the neurons in the graft had accumulated aberrant immunoreactivity similar to that found in and around degenerating neurons in Alzheimer's disease.

Specifically, thioflavin S, a histological marker for amyloid, showed positive staining within a few cells and around some blood vessels. In addition, antisera to the β-protein precursor, to β-protein itself, to ACT, to PHF, and to phosphorylated epitopes of tau labeled a few percent of cells in the trisomy 16 grafts. There was also some extracellular staining for ACT and β-protein precursor. When dissociated cells from trisomy 16 embryos were transplanted, the effects were not observed, suggesting that cell-cell interaction or cell degeneration in the bulk trisomy 16 tissue grafts used by Richards and her colleagues may be necessary for the neuropathology to develop. Interestingly, although β-protein precursor RNA was overexpressed approximately two-fold in trisomy 16 fetal mouse brains, it was overexpressed five-fold in the brains of chimerio (mosaic) mice having 40–50% trisomy 16 cells, again suggesting that a complex cell-cell interaction, affects the expression of this gene (Holtzman, et al., *Soc. Neurosci. Abs.* 469.6 (1990)).

The most recent link between Alzheimer's disease and chromosome 21 is evidenced by reports of two women whose lymphocytes were found to be mosaic for trisomy 21 and who, though not mentally retarded, had developed Alzheimer-like dementia by age 40 (Schapiro, et al., *Neurology* 39 *Suppl.* 1:169 (1989); Rowe, et al., *Lancet* Jul. 22,:229 (1989); for discussion, see Hardy, et al., *Lancet* Sep. 23:743 (1989)). In one case the woman also had a Down syndrome child. An unusual family with an inherited aberrant chromosome 22-derived marker chromosome was found by Percy M. E., et al., *Am. J. Med. Genet.*, (1991) to also have a high frequency of Alzheimer's disease. The two living affected members of the family carried the marker chromosome and one was also found to be mosaic for trisomy 21; only lymphocytes were analyzed from the other patient (see relevant discussion below). The two patients reported by Schapiro and Rowe and their colleagues and possibly the mosaic individual reported by Percy and her colleagues demonstrate that it is not necessary for every cell of an individual to be trisomy 21 for the aberrant effects of this chromosome imbalance to result in early Alzheimer dementia. The later onset dementia of classic Alzheimer's disease could thus result from an even smaller percentage of trisomy 21 cells that may go undetected.

Our proposal, that Alzheimer's disease and Down syndrome result from unequal chromosome 21 segregation in somatic and germ cells respectively, reconciles a seemingly diverse body of literature. For instance, one immediate implication is that any genetic or environmental factor that increases the chances of forming chromosome 21 trisomic cells should increase the likelihood of developing Alzheimer's disease. Thus, in the families in which the disease is apparently inherited as an autosomal dominant mutation near the centromere of chromosome 21, the mutation probably resides in the centromere itself so as to cause an increased frequency of nondisjunction of chromosome 21. During mitosis, such nondisjunction would build up trisomy 21 somatic cells, eventually leading to Alzheimer's disease pathology, while during meiosis it would generate trisomy 21 germ cells and Down syndrome offspring, as consistent with the epidemiological evidence. Indeed, there are centromere mutations known in yeast that result in a 100-fold increase in chromosome nondisjunction (Gaudet and Fitzgerald-Hayes, *Mol. Cell. Biol.* 7:68–75 (1987)).

Of course chromosome segregation is a complex process under the control of many gene products (for review, see Murray and Szostak, *Annu. Rev. Cell. Biol.* 1:289–315 (1985)), and an inherited disorder of chromosome segregation could be caused by mutations at a number of loci. In this light, the fact that familial Alzheimer's disease appears to be genetically heterogeneous is not surprising, since any one of several mutations could lead to the development of trisomy 21 cells, both somatic and germline, with the consequent development of Alzheimer's disease in the individual and an increased frequency of Down syndrome offspring. Several researchers have suggested that a specific microtubule defect could lead directly to the neuronal pathology and indirectly to the increase in Down's offspring in Alzheimer's disease through chromosome nondisjunction (Heston and Mastri, *Arch. Gen. Psychiatry* 34:976–981 (1977); Nordenson, et al., *Lancet* Mar. 1,:481–482 (1980); Matsuyama and Jarvik, *Proc. Natl. Acad. Sci.* 86:8152–8156 (1989).

Although improper chromosome segregation can result from a genetic mutation, it can also be caused by environmental agents. Of the many exogenous factors that influence chromosome segregation, microtubule-disrupting agents such as colchicine and low doses of radiation are perhaps the best studied (see, for example, Uchida, et al., *Am. J. Hum. Genet.* 27:419–429 (1975)). Aluminum, the consumption of which shows a weak, but significant association with the development of Alzheimer's disease (see, for example, Martyn, et al., *Lancet* 14 January:59–62 (1989)), also binds to microtubules and, in the form of aluminum silicate, causes chromosome nondisjunction in cultured cells (Paleker, et al., *Carcinogen* 8:553–560 (1987); for discussion see Ganrot, *Environ. Health. Persp.* 65:363–441 (1986)). Thus, the large proportion of Alzheimer's disease cases that arise in a sporadic manner not directly attributable to the inheritance of a genetic mutation can also be understood in the light of the chromosome 21 trisomy model.

An important prediction of this model is that it is the dividing cells in an individual that are most likely to develop chromosome 21 trisomy and lead to Alzheimer's disease. Extensive analysis by Rakic, *Science* 227:1054–1056 (1985) has shown that the only dividing cells in the brains of adult monkeys exposed to $^3$H-thymidine are glial cells and the endothelial cells lining blood vessels, while neurons, the cells most apparently affected by Alzheimer's disease, do not divide. The labeled glia were seen primarily in the hippocampus and the cerebral cortex. Thus cell division in the brains of adult primates occurs in those general regions that develop neuropathology in Alzheimer's disease, Down syndrome, and normal aging. Interestingly, astroglia in the hippocampus and cortex of Alzheimer's disease brain overexpress ACT, and astrocytes can be induced by kainic acid lesions to overexpress the B-protein precursor (Pasternack, et al., *Am. J. Pathol.* 135:827–834 (1989); Siman, et al., *Neuron* 3:275–285 (1989); for discussion of how overexpression of ACT or B-protein precursor can lead to amyloid formation, see Abraham and Potter, *Biotechnology* 7:147–153 (1989)).

Recently, two rapidly dividing peripheral tissues (skin and intestinal mucosa) have been reported to contain pre-amyloid deposits of β-protein in sporadic Alzheimer patients and some aged, normal subjects (Joachim, et al., *Nature* 341:226–230 (1989)). Another region of active cell division, which has been shown to exhibit pathological changes in Alzheimer's disease, is the olfactory epithelium. Thus there seems to be a rough correlation between regions of cell division and areas where Alzheimer pathology can develop. Of course, mitotic nondisjunction could also occur early enough in embryogenesis to generate trisomy 21 in nondividing adult cells such as neurons.

Although it would seem reasonable that amyloid should develop in the regions, immediately surrounding aberrant cells (for instance trisomy 21 cells), the precedent provided by other amyloidoses suggests that this need not be the case. For instance, the autosomal-dominantly inherited diseases Familial Amyloidotic Polyneuropathy and Hereditary Cerebral Hemorrhage with Amyloidosis of both the Dutch and Icelandic types have very specific regions of amyloid deposition despite the fact that all cells in the body carry the point mutation in the affected amyloid gene (transthyretin, cystatin C, or β-protein precursor, respectively), and that these genes are expressed in many parts of the body where the amyloid does not deposit (for review see Castano and Frangione, *Lab. Invest.* 58:122–132 (1988)). Thus, by analogy, the trisomy 21 cells that are relevant for the formation of amyloid pathology in Down syndrome (and, according to the hypothesis, Alzheimer's disease) need not reside in the brain at all. Indeed, some researchers believe that the β-protein is transported to the brain by the circulation, having been generated elsewhere (see, for example, Selkoe, *Neurobiol. Aging* 10:387–3395 (1989b) for recent data and discussion).

In sum, both genetic and sporadic forms of Alzheimer's disease can be explained as arising from the effects of trisomy 21 cells accumulating during the life of the individual. A propensity to develop such cells can be genetic in origin (either due to an aberrant chromosome 21 centromere or to a mutation elsewhere in the genome affecting all chromosome segregation), or it can be caused by environmental factors. A combination of genetic and environmental influences on the formation of trisomic 21 cells is responsible for the observed variation in the age of onset of Alzheimer's disease in identical twins and in Alzheimer's disease families. In addition, the fact that almost 50% of the population over the age of 85 show some symptoms of Alzheimer's disease dementia (Evans, et al., *JAMA* 262:2551–2556 (1989)), and an even larger proportion show some of the same neuropathological lesions, indicates that all individuals may, to some degree, be subject to stochastic events that lead to aberrant chromosome segregation with increasing age. The possibility that further biochemical or genetic events may be required before full Alzheimer neuropathology arises is indicated by the mature age (20's to 30's) that Down syndrome patients begin to accumulate amyloid deposits.

Cytogenetic analysis of Alzheimer's disease patients has been carried out in a number of laboratories, with mixed reports of increased aneuploidy or other abnormalities as measured directly (Jarvik, et al., *Arch. Gen. Psychiat.* 30:186–190 (1974); Ward, et al., *Am. J. Med. Genet.* 3:137–144 (1979); Nordenson, et al., *Lancet* Mar. 1:481–482 (1980); White, et al., *Am. J. Med. Genet.* 10:77–89 (1981); Buckton, et al., *J. Med. Genet.* 20:46–51 (1983); Moorhead and Heyman, *Am. J. Med. Genet.* 14:545–556 (1983)). Furthermore, premature centromere division (PCD), a correlate and potential cause of improper chromosome segregation in vitro and in vivo, was found to be positively correlated with age and to be increased in women with familial Alzheimer's disease (3.6% vs. 0.6% in age-matched controls), particularly affecting the X chromosome (Fitzgerald, et al., *Ann. Hum. Genet.* 38:417–428 (1975); Moorhead and Heyman, *Am. J. Med. Genet.* 14:545–556 (1983)). Trisomy 21, 18, and X occurred in the lymphocytes and fibroblasts of a woman apparently prone to PCD, who also had three trisomy conceptuses (Fitzgerald, et al., *Hum. Genet.* 72:58–62 (1986)). Patients with Roberts syndrome, a rare autosomal recessive disorder characterized by growth and mental retardation and craniofacial abnormalities, also shows PCD—there can be significant aneuploidy, usually involving chromosome loss rather than gain (except for trisomy 7) (see Romke, et al., *Clin. Genet.* 31:170–177 (1987). PCD can also be found that appears limited to the X chromosome and results, presumably by nondisjunction, in many cells with one or three X chromosomes (Fitzgerald, et al., *Ann. Hum. Genet.* 38:417–428 (1975)). Other Roberts syndrome families with extensive PCD have been found that exhibit normal karyotypes and phenotypes (Madan, et al., *Hum. Genet* 77:193–196 (1987)). Thus PCD need not result in nondisjunction, but when it does, severe developmental abnormalities can result if the autosomes are affected. The report by Fitzgerald and his colleagues (1986) is the only case of PCD in which trisomy of chromosomes other than the X chromosome were prevalent. Why Roberts syndrome generally results in chromosome loss rather than gain is not clear. Perhaps because of the severe mental retardation exhibited by these patients, neurological and pathological tests for Alzheimer's disease have not been reported.

The fact that the chromosomes that exhibit PCD in an individual do not necessarily correspond to those which ultimately are lost or gained to give an aberrant karyotype (there is a prevalence of trisomy 21, 18 and X in the general PCD case of Fitzgerald, et al., *Hum. Genet.* 72:58–62 (1986)), probably reflects differential cell viability. For instance, lymphocyte cultures from trisomy 21 mosaic individuals often show a lower proportion of trisomy cells than do, for instance, fibroblast cultures, and some patients with over 10% trisomy fibroblasts can show a normal karyotype in lymphocytes (out of, for example, 30 metaphases) (Pagon, et al., *Am. J. Hum. Genet.* 31:54–61 (1979).

Thus, the fact that cytogenetic studies on Alzheimer patients have almost always relied on peripheral blood lymphocytes (for example Jarvik, et al., *Arch. Gen. Psychiat.* 30:186–190 (1974); Ward, et al., *Am. J. Med. Genet.* 3:137–144 (1979); Nordenson, et al., *Lancet* Mar. 1:481–482 (1980); White, et al., *Am. J. Med. Genet.* 10:77–89 (1981); Buckton, et al., *J. Med. Genet.* 20:46–51 (1983); Moorhead and Heyman, *Am. J. Med. Genet.* 14:545–556 (1983)) may have prevented trisomy 21 mosaicism from being detected and linked to Alzheimer's disease. In these studies, fewer than 100 or even 50 lymphocyte metaphases per sample were examined, and the few percent with increased aneuploidy (generally a loss) for any chromosome in Alzheimer's disease was usually not significantly different from controls. The specific frequency of trisomy 21 was too low to be useful or was not stated.

The mechanism proposed herein can be tested by analysis of dividing cells from affected areas of the brain—glia, endothelial cells of the meningeal and cortical vessels, and the olfactory epithelium and possibly of skin fibroblasts. Procedures have recently been developed (Lichter, et al., *Proc. Natl. Acad. Sci USA* 85:9664–9668 (1988); Fuscoe, et al., *Genomics* 5:100–109 (1989)) that allow the number of chromosome 21s to be counted in both metaphase and interphase nuclei. The methodology is based on in situ hybridization with, for instance, biotin-labeled chromosome 21-specific probes, that are then visualized by fluoresceine-labeled streptavidin. The advantage of this approach over standard cytogenetics is that both dividing and non-dividing cells can be studied, and, more important, the number of chromosomes in interphase nuclei in tissue sections can be counted (Lichter, et al., *Proc. Natl. Acad. Sci. USA* 85:9664–9668 (1988)). Because the number of cells that might harbor three copies of chromosome 21 in Alzheimer's brain or peripheral tissue might be very small, the finding of a small cluster of trisomy cells would be far more significant than the same number of cells found one at a time among a population of thousands of other cells after they have been disaggregated and induced to divide in culture to yield metaphase chromosome spreads. The large number of "normal" aged individuals that show some symptoms of Alzheimer's disease and some Alzheimer pathology (neurofibrillary tangles and amyloid deposits) will make it necessary to carry out careful comparisons between Alzheimer's disease patients and age-matched controls. Such an analysis would, of course, be made easier by concentrating on earlier onset (often familial) Alzheimer's cases. Although initial studies would seem to be best directed at searching for trisomy 21 cells in the brain, the possibility (discussed above) that Alzheimer amyloid deposits may arise from aberrant cells in the periphery suggests that a similar in situ hybridiztion analysis should also be carried out on various other tissues, for instance skin and the intestinal mucosa.

If Alzheimer's disease patients are found to be mosaic for trisomy 21, then we might expect them to exhibit some other abnormalities of Down syndrome in addition to dementia—for example, hypersensitivity to acetylcholine agonists and antagonists. Such characteristics, together with in situ hybridization for chromosome 21, form the basis of a diagnostic test for Alzheimer's disease.

Diagnosis for Alzheimer's disease before symptoms of dementia arise can be accomplished by determining whether the individual is indeed mosaic for trisomy 21. This can be carried out either directly by in situ hybridization as described above, or indirectly by measuring certain characteristics known to be associated with Down syndrome that arise due to the trisomy 21 nature of this disorder, and assay them for their presence in a suspected Alzheimer patient. Examples of such Down's patient features include Brushfield spots on the irises, hypersensitivity of heart rate, pupil contraction, and sweat production to acetylcholine agonists and antagonists. Many methods for monitoring hypersensitivity to cholinergic agonists and antagonists are well known in the art. In short, any characteristic of Down syndrome may be used as a basis for designing a diagnostic test for Alzheimer's disease.

One example of such a diagnostic test is set forth in the Exemplification section which follows. Specifically, it is shown below that the administration of the cholinergic antagonist tropicamide, when administered to individuals identified as probable Alzheimer's disease patients at a concentration having a minimal but detectable effect on non-demented individuals, results in a substantial percent change in pupil diameter when compared with an untreated eye of the same individual. More specifically, tropicamide was administered to probable Alzheimer's patients at a concentration of less than 0.1% (the specific concentration was 0.01%) and resulted in about a 2-fold or greater percent change in pupil diameter.

Because the data indicate that Alzheimer's disease is a mosaic form of Down syndrome due to nondisjunction (but perhaps during meiosis followed by nondisjunction early in development to yield normal cells), much Alzheimer's disease may be prevented by preventing the nondisjunction from occurring, including such approaches as avoiding environmental agents that cause translocation by inducing chromosome nondisjunction, treatment with agents that reduce spontaneous nondisjunction or that obviate the effects of environmental agents, and mitotic inhibitors such as colcemid or methyl benzimidazole-2-yl-carbamate. Such treatment might include, but is not limited to, heavy metal chelaters, antoxidants, and promoters of microtubule assembly. Drugs that improve chromosome segregation will include those that affect DNA toposiomerase II, or centromere binding proteins such as CBF1, or DYSi. An additional approach may be to treat patients with drugs to which trisomy 21 cells may be particularly sensitive in the expectation that they will be preferentially killed and thus no longer pose a threat to the patient. This may be accomplished by killing cells that have an excess of certain cell surface markers known to be increased in cells from Down syndrome patients due to the trisomy 21. These include the cell surface marker S14 and interferon-$\alpha$ receptor.

EXEMPLIFICATION

The mydriatic response to administration of the cholinergic antagonist tropicamide was studied in 5 patients diagnosed as probable Alzheimer's patients. In addition, 13 negative control patients who did not exhibit symptoms characteristic of Alzheimer's disease were included in the study.

Subjects had normal findings on a brief-neurological examination and a bedside neuro-ophthalmological examination that evaluated saccades, smooth pursuit, visual fields to confrontation and partial field optokinetic nystagmus. All subjects' pupils were examined for a narrow angle anterior chamber to eliminate subjects at risk for narrow angle glaucoma. Subjects were disqualified from participation if they had small pupils (less than 2 mm diameter), unusual pupil shapes, star cataracts or incipient cataracts that might affect accurate measurement of pupil diameter. All non-demented controls had normal findings on a short neuropsychological battery and no diseases of the central nervous system by history. Medication use in patients and controls was comparable. No subject was taking medications with known interaction effects with tropicamide.

Pupil diameter was measured using an Applied Science Laboratories video based, near infrared pupil center to corneal reflection system. This system, used to measure eye movements, also measures pupil diameter sampled continuously at 60 hertz. The system is non-invasive and requires no subject attachments or restraints. For this study, subjects were seated in a comfortable room with dim ambient illumination 1.5 m in front of a TV screen.

The subjects' pupils were imaged by the system as they sat viewing the TV screen set at a uniform low illumination. Subjects were directed to look at the center of the screen while the eye was initially imaged. Once the eye was adequately imaged and subjects had ample time to adjust to ambient illumination, a short calibration procedure was run to ensure accurate monitoring of subjects' eye position.

A very dilute solution of tropicamide (0.01%) was used to induce pupil dilation in this trial. Tropicamide in a solution strength of 0.5 to 1.0% induces maximal mydriasis in 20 to 40 minutes in normal healthy subjects. The short action time of this agent was chosen to limit the time required to reach a maximal mydriatic response. After baseline pupil measurements were determined for each eye, a single drop of the tropicamide solution was added to one of the eyes (randomly chosen). Pupil diameter data was sampled from both eyes for 30 second epochs over the course of an hour at 0, 2.5, 8, 15, 22, 29, 41 and 53 minute intervals. Between measurement epochs, subjects were shown segments from the video tape Fantasia in order to reduce anxiety, fatigue and boredom from sitting in a semidarkened room.

The percent change in diameter in the treated versus the untreated eyes was compared for all patients. Dependent variables consisted of the overall percent change from baseline in the treated and untreated eyes, and the percent change in treated and untreated eyes compared to baseline at each sampling interval. The Mann-Whitney one tailed test for all between group comparisons. The results of these experiments are summarized in the FIGURE which shows the pupil diameter measurements observed in the treated eyes of both probable Alzheimer's patients and non-demented controls. The pupil diameter determinations for untreated eyes of non-demented and probable Alzheimer's patients were substantially identical, These data demonstrate that the overall dilation effect seen in probable Alzheimer's patients was significantly greater than that observed in the non-demented controls. Data for probable Alzheimer's disease patients are significant at p<0.05 level beginning at 15 minutes. No differences were found for the untreated eye at any sampling epoch or for the mean change over the seven sampling epochs.

Equivalents

Those skilled in the art will know, or be able to ascertain using no more than routine experimentation, many equivalents to the specific embodiments of the invention described herein. These and all other equivalents are intended to be encompassed by the following claims.

I claim:

1. A method for detecting Alzheimer's Disease in an individual comprising:
   a) determining pupil diameter for both eyes of the individual;
   b) administering to one eye of the individual a cholinergic antagonist at a concentration sufficient to produce a detectable difference in pupil diameter in an individual without Alzheimer's Disease compared with an individual with Alzheimer's Disease;
   c) determining pupil diameter for both eyes of the individual at periodic intervals following the administration of the cholinergic antagonist; and
   d) comparing the pupil diameter of the eye treated with the cholinergic antagonist and the pupil diameter of the untreated eye at corresponding periodic intervals following the administration of the cholinergic antagonist, a substantial difference in the percent change in diameter between the treated and untreated eyes being diagnostic of Alzheimer's Disease.

2. The method of claim 1, wherein the cholinergic antagonist is administered in an amount determined to induce minimal, but detectable, mydriasis in an individual not afflicted with Alzheimer's Disease.

3. A method of claim 1 wherein the substantial change in pupil diameter of the one eye compared with the pupil diameter following administration of the cholinergic antagonist is at least about 10%.

4. A method of claim 2 wherein the cholinergic antagonist is tropicamide.

5. A method of claim 4 wherein the tropicamide concentration is less than about 0.1%.

6. A method of claim 5 wherein the tropicamide concentration is about 0.01%.

7. A method for detecting Alzheimer's Disease in an individual comprising:
   a) determining pupil diameter for one eye of the individual;
   b) administering to the one eye of the individual a cholinergic antagonist at a concentration sufficient to produce a detectable difference in pupil diameter in an individual without Alzheimer's Disease compared with an individual with Alzheimer's Disease;
   c) determining pupil diameter for the one eye of the individual at a time following the administration of the cholinergic antagonist suitable for detecting mydriasis in the one eye of the individual; and
   d) comparing the pupil diameter in step c) for the one eye with the pupil diameter determined in step a) for the one eye,
   wherein a substantial difference in the pupil diameter determined in step c) for the one eye compared with the pupil diameter determined in step a) for the one eye is diagnostic of Alzheimer's Disease.

8. The method of claim 7 wherein the cholinergic antagonist is administered in an amount determined to induce minimal, but detectable mydriasis in an individual who does not have Alzheimer's Disease.

9. A method of claim 8 wherein the substantial change in pupil diameter determined in step c) for the one eye compared with the pupil diameter determined in step a) for the one eye is at least about 10%.

10. The method of claim 8 wherein the cholinergic antagonist is tropicamide.

11. The method of claim 10 wherein the tropicamide concentration is less than about 0.1%.

12. The method of claim 11 wherein the tropicamide concentration is about 0.01%.

13. A method for detecting Alzheimer's disease in an individual who does not have the symptoms characteristic of Alzheimer's Disease comprising:
   a) determining pupil diameter of one or both eyes of the individual who does not have the symptoms characteristic of Alzheimer's Disease;
   b) administering to an eye, referred to as the treated eye, whose pupil diameter was determined in step a) a cholinergic antagonist at a concentration sufficient to produce a detectable difference in pupil diameter in an individual without Alzheimer's Disease compared with an individual with Alzheimer's Disease;
   c) determining pupil diameter for the treated eye at a sufficient period of time following the administration of the cholinergic antagonist for detecting mydriasis in the treated eye; and
   d) comparing the pupil diameter determined in step c) for the treated eye with the pupil diameter determined in step a) for one of the eyes,
   wherein a substantial difference in the pupil diameter determined in step c) for the treated eye compared with the pupil diameter determined in step a) for the one eye is diagnostic of Alzheimer's Disease in the individual who does not have the symptoms characteristic of Alzheimer's Disease.

14. The method of claim 13, wherein the cholinergic antagonist is administered in an amount determined to induce minimal, but detectable, mydriasis in an individual not afflicted with Alzheimer's Disease.

15. A method of claim 14 wherein the substantial change in pupil diameter determined in step c) for the treated eye compared with the pupil diameter determined in step a) for one of the eyes is at least about 10%.

16. The method of claim 14 wherein the cholinergic antagonist is tropicamide.

17. The method of claim 16 wherein the tropicamide concentration is less than about 0.1%.

18. The method of claim 17 wherein the tropicamide concentration is about 0.01%.

19. A method for aiding in the diagnosis of Alzheimer's disease in an individual comprising:
   a) determining pupil diameter of one or both eyes of the individual;
   b) administering to an eye, referred to as the treated eye, whose pupil diameter was determined in step a) a cholinergic antagonist at a concentration sufficient to produce a detectable difference in pupil diameter in an individual without Alzheimer's Disease compared with an individual with Alzheimer's Disease;
   c) determining pupil diameter for the treated eye at a sufficient period of time following the administration of the cholinergic antagonist for detecting mydriasis in the treated eye; and
   d) comparing the pupil diameter determined in step c) for the treated eye with the pupil diameter determined in step a) for one of the eyes,
   wherein a substantial difference in the pupil diameter determined in step c) for the treated eye compared with the pupil diameter determined in step a) for the one eye indicates that the individual should be tested further for Alzheimer's Disease.

* * * * *

UNITED STATES PATENT AND TRADEMARK OFFICE
CERTIFICATE OF CORRECTION

PATENT NO. : 5,535,760
DATED : Jul. 16, 1996
INVENTOR(S) : Huntington Potter

It is certified that error appears in the above-indentified patent and that said Letters Patent is hereby corrected as shown below:

Col. 1, The second paragraph of the text of the Patent should read:

-- Government Support

This invention was made with government support under Grant Nos. AG08084 and GM35967 by the National Institutes of Health. The government has certain rights in the invention.--

Claim 3, line 25: delete "1" and insert --2--.

Signed and Sealed this

Nineteenth Day of May, 1998

Attest:

BRUCE LEHMAN

*Attesting Officer*   *Commissioner of Patents and Trademarks*